United States Patent
Brinton, Jr. et al.

(10) Patent No.: US 9,090,497 B2
(45) Date of Patent: Jul. 28, 2015

(54) MODULAR, SCALABLE HIGH SOLIDS METHANE DIGESTER FOR SMALL-SIZED TO MEDIUM-SIZED FARMS

(75) Inventors: William F. Brinton, Jr., Mount Vernon, ME (US); Jeffrey H. Bragg, Sidney, ME (US)

(73) Assignee: Jeffrey H. Bragg, Sidney, ME (US)

( * ) Notice: Subject to any disclaimer, the term of this patent is extended or adjusted under 35 U.S.C. 154(b) by 491 days.

(21) Appl. No.: 13/484,957

(22) Filed: May 31, 2012

(65) Prior Publication Data

US 2013/0319937 A1    Dec. 5, 2013

(51) Int. Cl.
| | | |
|---|---|---|
| *C02F 11/04* | (2006.01) | |
| *C02F 1/00* | (2006.01) | |
| *C02F 11/12* | (2006.01) | |
| *C02F 103/20* | (2006.01) | |

(52) U.S. Cl.
CPC ............ *C02F 11/04* (2013.01); *C02F 1/001* (2013.01); *C02F 11/121* (2013.01); *C02F 2103/20* (2013.01); *C02F 2201/007* (2013.01); *Y02E 50/343* (2013.01)

(58) Field of Classification Search
CPC ........ C02F 11/04; C02F 1/001; C02F 11/121; C02F 2103/20; C02F 2201/007; Y02E 50/343
USPC .................. 210/603; 52/272, 282.3, 284, 294
See application file for complete search history.

(56) References Cited

U.S. PATENT DOCUMENTS

| | | | | |
|---|---|---|---|---|
| 3,747,287 | A * | 7/1973 | Finger | 52/18 |
| 5,285,914 | A * | 2/1994 | Del Zotto | 220/4.12 |
| 5,562,759 | A * | 10/1996 | Morgan et al. | 96/155 |
| 6,009,677 | A * | 1/2000 | Anderson | 52/251 |
| 2004/0093810 | A1* | 5/2004 | Mooney | 52/177 |
| 2007/0266651 | A1* | 11/2007 | Harig et al. | 52/169.6 |
| 2008/0085548 | A1 | 4/2008 | Lutz | |
| 2008/0098676 | A1* | 5/2008 | Hutchens | 52/281 |
| 2008/0299634 | A1 | 12/2008 | Lutz | |
| 2009/0239209 | A1 | 9/2009 | Lutz | |
| 2010/0068792 | A1 | 3/2010 | Lutz | |
| 2010/0155313 | A1* | 6/2010 | Wilson et al. | 210/98 |
| 2010/0159571 | A1 | 6/2010 | Lutz | |
| 2010/0311141 | A1 | 12/2010 | Lutz | |
| 2014/0061106 | A1* | 3/2014 | Knoop | 210/96.1 |

* cited by examiner

*Primary Examiner* — Fred Prince
(74) *Attorney, Agent, or Firm* — Brown & Michaels, PC

(57) ABSTRACT

A modular methane digester facility includes prefabricated portable concrete panels and a flexible membrane roof sealing an interior space of the methane digester. A separator-conveyor dewatering device, integratable into the front end of the methane digester facility, separates a semi-solid liquid manure into a liquid portion and a solid portion. A method of dual-stage methane digestion includes stacking a solid stage in a methane digester and supplying a liquid stage to the top of the solid stage. The liquid stage percolates by gravity through the solid stage, the solid stage acts as a filter for the liquid stage, and the liquid stage acts as a methanogenic buffer for the solid stage. A method of pre-heating a mass of solids in a methane digester to a mesophilic temperature includes supplying oxygen to the mass of solids in the form of ambient air supplied to the methane digester by a reverse-air pump.

9 Claims, 8 Drawing Sheets

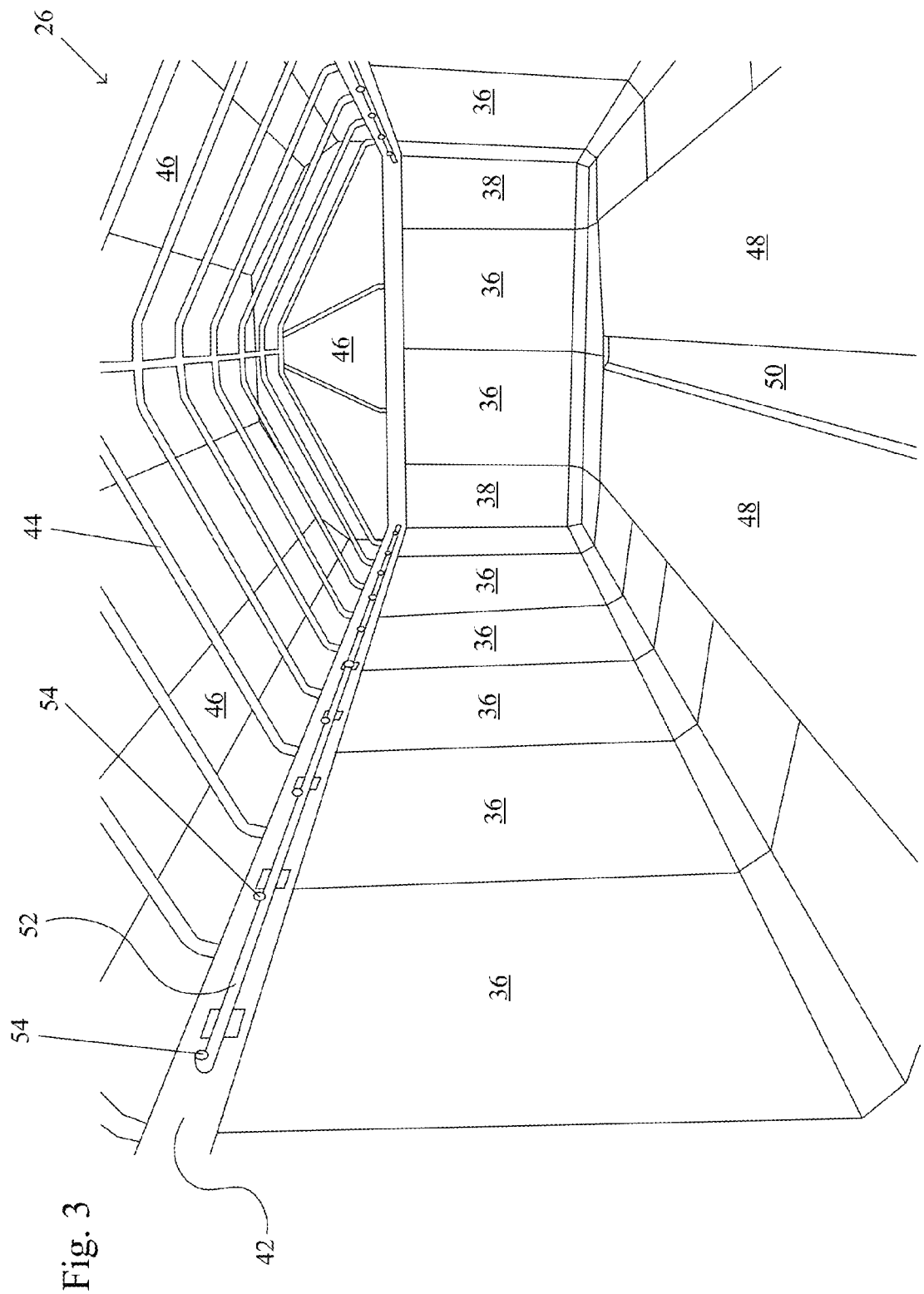

MODULAR, SCALABLE HIGH SOLIDS METHANE DIGESTER FOR SMALL-SIZED TO MEDIUM-SIZED FARMS

BACKGROUND OF THE INVENTION

1. Field of the Invention

The invention pertains to the fields of agriculture and energy production. More particularly, the invention pertains to systems, methods, and structures for the production of biogas for heat and energy recovery from on-farm animal and plant residues.

2. Description of Related Art

Biogas production is a common feature on many farms worldwide, whereby the methane content is employed as the source of combustible energy. Farmers may customarily produce methane by exclusion of air inside sealed containers to produce a mixture of fermented gaseous byproducts as biogas. It has become very common to construct liquid-based manure systems in which outflow of daily farming operations, including manure wash and barn milk parlor, washes together with miscellaneous farm residues such as hay, straw and spent silage and feed. These mixtures are pushed or gravity-fed into cement in-ground tanks, in which, by applying elevated temperature and swirling action, rapid methanogenesis occurs by nature of the bacteria in the mixture indigenous to the gut of ruminants, especially cows. The net result is the production of gas, in particular methane-enriched gas.

It is possible within a dairying operation to run a digester with no requirement for any outside inputs, save only the manure in liquid form. Some dairies supplement digesters by adding fermented milk solids waste, yogurt waste, whey from cheese-making and the like, even to the extent of adding pulped or slurried food waste from area sources. In virtually all of these cases, the normal function of the digester is maintained so long as the flow characteristics of the influents and effluents are held within normal boundaries, as defined by pipe and trough volume and flow restraints. If the material becomes too thick, as from heat evaporation of manure in summer while on the floors or from inclusion of wastes that have elevated solids content, then wash water, water, or similar very low solids liquid is added to maintain consistency. The result of the liquid-based approach on farms is massive lined-steel or concrete tanks requiring a sizable capital input.

Methane is the common desired product of anaerobic fermentation of organic residues, whereby both carbon dioxide ($CO_2$) and methane ($CH_4$) are formed, together called biogas. Other smaller components of biogas are water ($H_2O$) and hydrogen sulfide ($H_2S$). Inoculums other than manure are uncommon. Manure that is allowed to stand outdoors in a pile may have a reduced methane content as a result of poisoning of methanogens by the presence of regular air, in particular by the presence of gaseous oxygen.

The methane process requires a certain period of time to go through stages of anaerobic decomposition to achieve the resulting methane-enriched gas. This time period may vary in terms of mean residence times in the range of 5 days to 30 days. While ruminant manure is ideally predisposed for methane formation, the addition of quantities of other waste, including straw, silage, and food scraps, necessitates a pre-fermentation for the breakdown into component fatty acids, especially acetic acid, a direct precursor of methane gas. This may constitute a lag phase of one to several days, and if the feed stream is loaded improperly or excessively with outside ingredients, may dispose the reactor to sourness or pH crashes, recovery from which certainly meaning lost time in digestion. Maintaining swirling or moving action in order to maintain contact between freshly input materials and those already fermented in the tank is very important to provide a buffering action that helps eliminate swings in fermentation performance and behavior. On some occasions buffering agents, such as bicarbonate, are added to input materials, such as food scraps, to avoid excessive punch down in biological activity in the tank.

An additional and significant problem with liquid-based systems, in addition to requiring massively sized tanks, is that the entire farm must essentially convert to liquid-based materials and flows and must maintain a farm disposal system for the liquid effluent resulting from the digestion process. Effluent production is a daily phenomenon of a liquid system, and storage space for liquid effluent is limited. Storage of effluent, in fact, typically requires more tanks and holding capacity, and while not strictly aerobic after coming out of the digester, the open tanks continue to emit background or fugitive methane, which is a significant atmospheric global deterrent and often cited as a negative carbon balance for dairying. Rapid incorporation, therefore, of liquid effluent into surface soils, which by nature of being very aerobic, reduces any further methane output to a minimum and is the only practical solution to the problem. Such action is not a very feasible option to farmers during the winter and summer seasons because of limited access to useable surface soil together with environmental regulatory restrictions. In winter in colder climates, frozen ground greatly limits or prevents uptake of the effluent. During the growing season, the presence of agricultural crops and pasturing preclude addition of fresh waste liquids to many areas. Excess storage of liquid effluent, in addition to influent manure, creates the potential for overflow and entrance to surface and groundwater, particularly in inclement seasons with poor weather and above-average rainfall. The pernicious cycle of open-air liquid systems fostering liquid restraints, sensitivity to rainfall excess that causes overloading of lagoons, and environmental damage from leaked fugitive gases and nutrient contamination of waterways from these liquids poses real constraints to the liquid-based theory of methane digestion.

Construction of large, in-ground, heated concrete tanks to handle the liquid effluents is a real cost constraint for dairy farms, and it has been proposed by many that liquid methane systems are not viable for farms with under 500 head of cattle. It is, however, well known that methane biology is extremely scalable, meaning that the fermentation process is not, in fact, limited by size and there is no efficiency of scale pertinent to the biology. Medium or smaller farms number in the thousands in America, yet methane digestion technologies, by the nature of focusing on a minority of large to very large dairy farms, such as 2,000 to 5,000 head operations, have thereby effectively excluded provisions for medium and small farmers of cost-effective environmental solutions to manure and waste handling, and therefore have hampered America's ability to expand energy-efficient futures.

Most farms would prefer to have an opportunity to better handle waste, and especially to produce energy if cost effective, as farms require a constant flow year round of both fuel and electricity. Biogas, once produced, may be used as unfiltered, uncompressed gas for boilers and heating and may also be fed to engines for direct conversion to electricity, or the combined heat and power (CHP) units to produce heat and electricity simultaneously. Also, biogas, once cleansed of excess water, hydrogen sulfide and carbon dioxide, may be prepared as compressed natural gas (CNG, also referred to as compressed biogas or CBG in Europe) and used to co-fuel farm diesel tractors and other vehicles, as a primary fuel source, a conversion that is increasingly practiced in the world. Since the majority of the world's farms are medium to small scale, the absence of viable methane technologies for small scale approaches means that common solutions to increase viability and sustainability of farm operations from an energetic and cost-effective point of view are lacking.

While many very small farms in third-world regions have addressed the situation by design and construction of small to very small digester systems run almost entirely by manual farm hand labor, small farms in industrialized nations do not have such hand labor available and have not chosen to build these very flexible, small-scale systems. There is an evident gap in the farm energy methane digester capable of providing for a family farm of one to four cows or llamas or 10-30 sows, such as are common in developing nations and third world regions, and those small farms in the United States, which may have in the range of 75-300 cows, in other words large by third-world standards, but in fact small by western-world modern standards. It is this gap that the current systems, methods, and structures propose to fill.

Most of the commercial industrial engineering firms that design and construct farm methane digesters are trapped in this costly and somewhat environmentally unfriendly struggle to handle on-farm liquid wastes and provision of electricity and heat energy to large and super-sized farms, where undoubtedly the biogas solution is better than no action at all. It does not solve the liquid handling problems and it entails huge capital reserves and debt to cover costs. Additionally, in many regions the concept of public purchase of excess electricity generated by these large 100-500 kW systems is not sufficiently developed other than an offer of net metering to farm owned facilities or recapture by utility companies at grossly devalued worth, meaning the energy creation from methane is not a very viable path. The efficiency of gas-to-electricity conversion, being as low as 35%, and the cost-effectiveness of such electricity generation in view of sometimes poor returns on sold or net-metered electricity, in addition to requiring a significant capital investment in energy generation units, also restricts the usefulness of the electricity approach. Creating a cost-effective methane system, however, within a small farm environment, where a focus on heat production from biogas, which is much more efficient at 70-90% efficiency, and cleansing and compressing for vehicular on-farm use as transport fuel, may make it more sustainable than larger systems that convert the biogas to electricity.

The liability for over-sized, over-designed farm energy production operations falls almost entirely on the farmers themselves, as engineers and investors rarely assume management positions in on-farm systems, and failure therefore is the sole risk of the farmers as well, this coming at a time when on-farm debt has grown disproportionately to farm sustainability. This is very costly to society as a whole, since failure of farms inevitably drives up costs of food and results in more environmental destruction from larger and super-sized farming operations.

SUMMARY OF THE INVENTION

A modular methane digester facility includes prefabricated portable concrete panels and a flexible membrane roof sealing an interior space of the methane digester. A separator-conveyor dewatering device, integratable into the front end of the methane digester facility, separates a semi-solid liquid manure into a liquid portion and a solid portion. A method of dual-stage methane digestion includes stacking a solid stage in a methane digester and supplying a liquid stage to the top of the solid stage. The liquid stage percolates by gravity through the solid stage, the solid stage acts as a filter for the liquid stage, and the liquid stage acts as a methanogenic buffer for the solid stage. A method of pre-heating a mass of solids in a methane digester to a mesophilic temperature includes supplying oxygen to the mass of solids in the form of ambient air supplied to the methane digester by a reverse-air pump.

BRIEF DESCRIPTION OF THE DRAWINGS

FIG. 3 shows schematically a completed interior of a modular methane digester in an embodiment of the present invention.

DETAILED DESCRIPTION OF THE INVENTION

Figure 1:
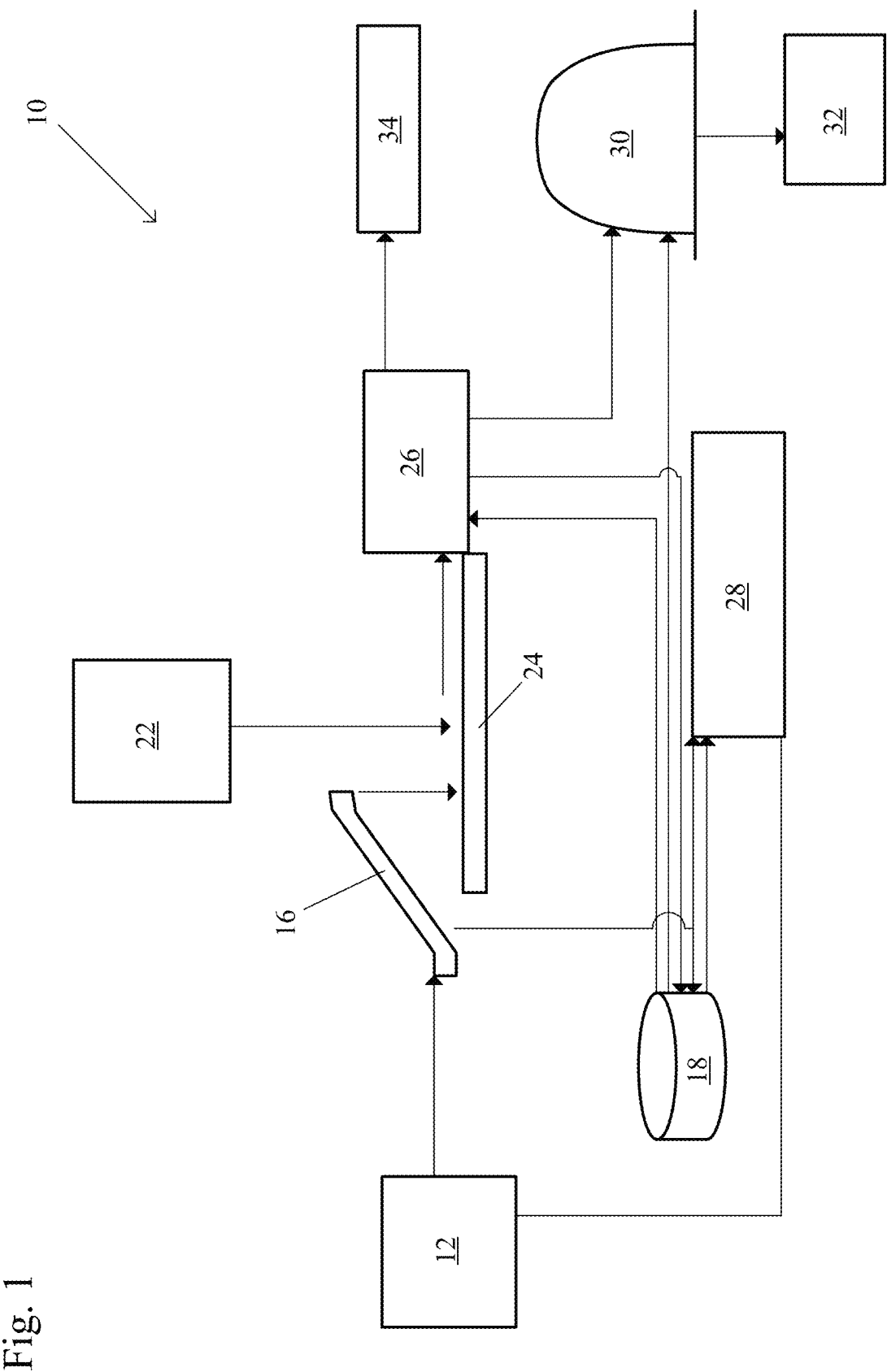
FIG. 1 shows schematically a methane digestion system in an embodiment of the present invention.

The integrated modular expandable design approach to methane production is space-efficient, and therefore very cost-effective, and is highly suited to small-to-medium sized farms that have hitherto been overlooked for methane digesters.

In some embodiments, methods permit the modular construction of small-to-medium scale on-farm methane digesters that are expandable and inexpensive in comparison to conventional methane digesters.

In some embodiments, the modular construction of a small-to-medium scale on-farm digester is expandable and inexpensive in comparison to conventional methane digesters.

In some embodiments, construction complexity of on-farm digesters is reduced, making it feasible for farmer-only construction of the holding tanks, or bunkers, and the associated buildings.

The methane digester preferably incorporates prefabricated concrete panels as typically employed by farmers for silage bunker walls, thereby making it modular, flexible, and expandable.

The prefabricated modular units are preferably placed in such a configuration as to produce two side walls connected by a back wall. A sealed membrane roof integrated into a sealed door complete the basic structure of the methane digester.

In some embodiments, concrete headers are placed onto the top walls of modular panel units so that all are effectively tied together.

The modular units are preferably sealed to be gas-tight by a membrane cover preferably made of elastic rubber and silicon. The top headers are also preferably sealed so as to be seated gas-tight onto the modular wall units.

In some embodiments, the modular facility is covered with a non-permeable methane-trapping membrane that is capable of collecting and holding the biogas above the facility.

In some embodiments, a flexible gas-tight expandable rubber membrane is passed over the mass and obviates the need for concrete roof encasements.

In some embodiments, the methane digester includes a gas-tight membrane roof suspended over the open area of the digester on a modular PVC pipe lattice. The lattice preferably snaps into the tops of concrete modular wall units, in which receiving points have been inserted.

In some embodiments, tie-in posts suitable for holding and taking a modular light-weight plastic PVC (polyvinyl chloride) pipe roof are inserted into the concrete headers. In some embodiments, the modular PVC pipe roof system rests inside the edges of the rubber membrane enclosure as a channel, which clamps and seals the rubber membrane enclosure onto the header units in a manner to prevent air input or gas egress.

In some embodiments, a modular concrete angled front piece produces a sloped door inset piece, when placed and connected into the modular side panel units. A membrane door closure fixture to permit access to the interior of the methane digester is preferably connected to the door inset piece.

In some embodiments, a collapsing modular door unit includes loosely attached membrane and lowers and seals off the front of building.

The membrane roof-door unit is preferably formed to be capable of withstanding pressures of at least about 6-in. static water pressure, 0.25 PSI, 4 ounces, 0.015 bar, or 1,500 Pascals.

In some embodiments, wood planks are placed in recessed concrete channels facing each side angled wall and located toward the front of the bunker to prevent manure from seeping into the door area.

In some embodiments, gas storage bags are maintained inside silos to maintain a constant gas pressure.

In some embodiments, the modular construction of a methane digester facility includes placing portable movable concrete panels to form a pair of opposing side walls and a back wall connecting the side walls. The modular construction further includes forming a front wall opposite the back wall from a modular concrete angled front piece to produce a sloped door inset piece. The modular construction also includes sealing an interior space of the methane digester using a flexible, expandable membrane roof across the tops of the walls, a plurality of headers between the panels, and a flexible door over the sloped door inset piece. The modular construction allows the methane digester to be scaled and expanded to suit the needs of a particular farm.

In some embodiments, the methane production is accomplished in a dual-stage process including a solid stage and a liquid stage. The solid stage includes a moisturized solid mass, and the liquid stage is a fully liquid state. The solid stage material becomes naturally stackable, thereby enabling a phase of solids digestion not previously performed. Each of the two stages preferably supports the other in multiple "holistic" ways. For example, a solid stage is conventionally considered non-conducive to efficient methane generation, but a liquid phase, while efficient for methane, is not so if the solid content is too low such that the methane generation rate per unit volume is very low, a reason for the very high cost of structural elements in a strict liquid system. In some embodiments, the low solid content of the liquid is an asset and not a hindrance, and the solidness of the solid phase is an asset, as it enables the liquid to flow through it, imparting microbial methanogenic properties to the entire mass, replacing exhausted bacterial cells, and re-inoculating the mass. In some embodiments, the high solids content of the solid mass is an asset by imparting a filtering function respective of the percolate so that the drainage is relatively free of suspended solids and organic fragments that may otherwise tend to clog systems. This form of dual-system digester has not been previously considered for methane production.

In some embodiments, the solid stage is created by removal of excess manure liquid using a mechanical conveyance device augmented by air blasts prior to loading the solid stage into the digester.

In some embodiments, the interaction of the two stages is in the form of a temporarily combined state of a liquid-solid mass of about 20-30% solids which is stacked inside a modular constructed bunker.

In some embodiments, a wide range of normal on-farm wastes not normally digested in liquid systems may be added to the methane digester regardless of the solids content. Any liquid portion of any farm waste stream may be percolated into and over the solid stage mass such that the liquid portion contributes its own methane potential and is kept within the closed cycle.

In some embodiments, any other liquid fermentable material, including, but not limited to, whey, liquid sugar, and milk solids, may be added into the liquid percolate stream, separately and distinctly from the solids mass.

In some embodiments, any dissolved fermentable organic waste may be directly added into the percolate digester tank so that it may be percolated over the entire fermenting solids mass, which adds to the overall energy capture of the facility.

In some embodiments, dual stage digestion of a solids mass and a liquid fraction is achieved by interacting the two stages in a percolate filtering system. Each stage supports and fortifies the other. The solid stage acts as a filter to the liquid stage, and the liquid stage acts as a methanogenic buffer for the solid stage, enabling it to become a "sour dough" starter for the subsequent batches that are added in cycles to the digester. The methane digester acts in some ways as two complete digesters, the one piggy-backed on top of the other.

In some embodiments, the stacked solid mass of the first stage of the dual stage system, formed of on-farm manure and other on-farm ingredients, serves as a filter for the percolating liquid of the second stage, such that the percolate liquid digester tank is not encumbered and burdened with excess solids. The percolate trough inside and under the modular bunker is preferably filled with chipped marble ($CaCO_3$) gravel, which filters dissolved hydrogen sulfide ($H_2S$) out of the liquid stage solution by chemical reaction and captures the sulfur as insoluble calcium sulfide (CaS).

In one embodiment, the on-farm manure handling includes a water separation device, referred to herein as a separator-conveyor, such that manure voided by cows and scraped from floors at about 9 to 10% solids may be naturally and readily increased to about 20% solids. This enables stacking by conventional tractor handling equipment to meet the solid stage requirement for the dual-stage system. The manure composition for this solid stage is preferably of a stackable nature, which is roughly defined as having an elevated solids content or containing an abrasive content, such as hay and straw or waste silage and grain cleaning residues from routine farm operations that may be readily added without concern for insufficient liquid content in the existing manure mass. The separation trough material and the farm residue material, such as hay, straw, and silage already of a semi-solid nature, may be combined into the separated manure and preferably combined in a ratio such that the end product may be freely piled without slumping.

In some embodiments, a low-cost separator enables formation of an elevated solids manure that meets the solid stage requirement for the dual-stage system such that the resulting solid stage may be directly inputted by piling in the modular bunkers without the necessary addition of any other farm residues, although additions of soiled straw and hay or waste silage provide favorable structural components. During the separation process, excess moisture from the feed stream is moved by gravity to an air-sealed holding tank. The holding tank holds the liquid stage of the dual-stage system. The liquid stage later interacts with the solid stage by being pumped back over the solids mass and then percolating back into the liquid stage.

In some embodiments, after the correct solid stackable composition of manure and other residues is obtained, the excess liquid forming the liquid stage is percolated into the top of the solid mass in the modular bunker. The percolate then drains through the solid mass and confers its methanogenic properties to the solid mass. Although the solid mass already possesses methanogenic potential on its own, as a result of the manure from dairy animals, the solid mass is enhanced in its capacity to create biogas by the flow and trickle effect of the liquid portion of manure and other waste passing through the stacked mass.

The methane digester may operate with the two stages totally converging and sharing methanogenic properties, the two stages in diverging phases functioning separately, or the two stages nearly completely divergent with one stage in an ending phase and the other stage in a beginning phase.

In some embodiments, the percolated liquid from the modular bunker is transferred to a holding fermenter tank, which is interconnected into the biogas system and which also contributes as a liquid to overall biogas production, but which is also continuously percolated by nozzles over the solid mass, thereby completing a circulation cycle and necessary interaction of the solid and the liquid stages of the dual-stage system.

In some embodiments, the methane digester includes a set of pipe nozzles designed specifically to provide a spray arc pattern of liquid semi-solid percolate over the solid mass. The liquid semi-solid percolate then falls down into the solid stage, thereby efficiently spreading the liquid across the solid mass to provide consistent and evenly-distributed percolation.

In some embodiments, the percolate flow through the solid mass and its relative energy content is quantified by in-line $CO_2$ and $CH_4$ capture. The gases may be removed in polyvinyl fluoride (PVF) bags, such as those marketed under the trademark Tedlar® (E.I. Du Pont De Nemours and Company, Inc., Wilmington, Del., US), at this point in production, their precise composition preferably being determined by a gas chromatograph.

In some embodiments, the feed stream prepared for the digester is tested in order to determine that it is sufficiently solid and of sufficient biogas methane potential (BMP) as to be viable input material to the digester. This includes measuring the solids-to-organic matter ratio (TS:OM), whereby the upper water holding capacity (WHC) margin is known. The capability to hold a specific quantity of water, which establishes the optimal flow rate of percolate through the system, may be precisely determined at any one point in time from this data.

In some embodiments, the percolate collection system permits the liquid stage of the dual stage system to be continuously moved through the solid stage of the dual stage system. The seepage or percolation from the solid stacked mass of manure-plant matter mix is preferably returned to the liquid stage fermenter component of the dual stage system.

In some embodiments, the methane fermenter includes a percolate trough system. The percolate trough system is preferably filled with hydrogen sulfide-absorbing chipped marble. Marble is a form of calcium carbonate and is very sensitive to sulfidation, a process whereby dissolved hydrogen sulfide reacts with calcium carbonate to form calcium sulfide, a black-colored precipitate. The trough is preferably readily accessible for periodic removal of sulfide-laden stone. The sulfide-laden stone is preferably placed in moist air to convert the odorous sulfide back to a harmless sulfate ion, which may be used as a soil fertilizer or ornamental gravel in the form of calcium sulfate, or gypsum.

In some embodiments, the methane fermenter includes a nozzle system located on the upper edge of the modular walls to deliver aspirate or spray of percolate to drench the entire mass of manure mix residing on the bunker floor.

In some embodiments, the methane fermenter includes a separator-conveyor dewatering system to naturally increase the solids content of the wet manure. The separator-conveyor dewatering system may use paddles or air pressure, or both, to remove water from the moving conveyed manure. The system is preferably integrated into the front end of the digester and capable of removing excess moisture from manure in a manner significantly better and significantly lower in cost than conventional separators that are made to achieve very high solids for animal bedding, for composting, or for transportation off the farm. It is not necessary to achieve such a very high solids content for such a high-solids methane digester, but only to attain a stackable status of the manure, such that the system may be loaded by common farm equipment and liquid may be percolated through the course, stacked material.

In some embodiments, the solid digester spent material is treated inside or outside the modular bunker by immediately commencing aerobic infusion of air to return it to a non-methane emitting status by encouraging the growth of aerobes. The material may then be used in a saleable soil-amendment product.

In some embodiments, the ratio of dissolved organic acids-to-total inorganic carbonate (OA:IC) in the percolate stream is tested such that the health of the entire digester, including the bunker and the percolate digester, may be determined. If the health of the methane digester is determined to be poor, additional fermentable organic wastes such as whey or spent glycerol, or alternatively bicarbonates, may be added directly to the percolate tank to add to the overall energy recovery of the facility.

In some embodiments, the substantially solid digester output material, or spent digestate, may be handled using farm equipment, such as bucket loaders and manure spreaders, and may be immediately composted. Composting of the digester output material is a process of storage, which is aerobic and which reduces or eliminates the potential of methane fugitive emissions and preserves the nutrient value in a stable and non-environmentally objectionable form.

In some embodiments, the methane fermenter includes a port to force air up into the percolate trough. The port passes the air upwards into the manure mix to return and convert the manure mix to an aerobic state at the end of the methanogenic process.

In some embodiments, the methane digester is capable of pre-heating a mass of solids to mesophilic temperatures in the range of about 35 to about 40° C. by reason of aerating the solids content by way of a percolate trench in the floor and a reverse air-pump. The process serves two purposes, one being to bring the initial cool mass of solids up to temperature to speed the methane conversion, without the requirement for external heating, and the other being to enable the separate solids stage to be returned to an aerobic mesophilic state after digestion, which is suitable for exposure to air and use as a compost or fertilizer.

By provided the oxygen containing air to the mass, either before or after the anaerobic phase, exothermic (aerobic) respiration pathways are enabled for the microbial mass present, and heat generation commences. The heat generation from metabolism of available carbon compounds is generally formed as a result of the following reaction:

$$C_6H_{12}O_6 + 6O_2 \rightarrow 6CO_2 + 6H_2O + \text{energy};$$

with a Gibbs free energy (ΔG) of −2880 kJ per mole of $C_6H_{12}O_6$.

This heat generation does not happen from anaerobic metabolism due to the absence of oxygen. It is therefore convenient to apply this biochemistry principle and utilize air flow input containing oxygen to stimulate production of energy, in the form of heat. The production of energy in the form of heat is useful for start-up, as an intrinsic, low-cost means to heat the mass, and it is also useful at the end of the process, to provide an end material that appears and acts as compost and is considered a favorable soil amendment.

FIG. 1 shows a methane digestion system 10 in an embodiment of the present invention. Production animal waste from a production animal source 12 is transported as a semi-solid up a solids conveyor-separator 16, with the separated liquid traveling to a percolate storage tank 18 or alternatively, based on the demand of the digester, to a storage lagoon 28, while the remaining solids are transported to a mixing pad 24. The solids conveyor-separator 16 serves to raise the solids content in the flow stream. Additional solid waste from an animal solid waste source 22 is transported to the mixing pad 24, where it is mixed with the solids brought to the mixing pad by the conveyor-separator 16.

The mixed solids from the mixing pad 24 are supplied to the high solids digester 26, where an anaerobic environment promotes the formation of methane. Liquid waste from the percolate storage tank 18 is preferably percolated over the high solids waste in the high solids digester 26. Liquid waste runoff after percolation in the high solids digester 26 is maintained in a continuous cycle with the percolate storage tank 18 and excess is bled off to the storage lagoon 28. The methane produced in the high solids digester is transported to a gas storage dome 30 until needed in the gas-processor 32 as a fuel source for heat or electricity or to be compressed to form compressed natural gas (CNG). The spent solid waste from the high solids digester 26 is sent to a compost or field application site 34.

In one embodiment, the methane digestion system is scaled to process about 367 cubic feet of production animal waste and about 86 cubic feet of animal solid waste per day. The production animal waste is separated into about 73 cubic feet of solids and about 293 cubic feet of liquids per day. The 73 cubic feet of solids is combined with the 86 cubic feet of animal solid waste, and the combined 159 cubic feet of solids per day is supplied to the high solids digester and percolated by the liquids in the production of about 3,370 cubic feet of methane per day.

Figure 2A:
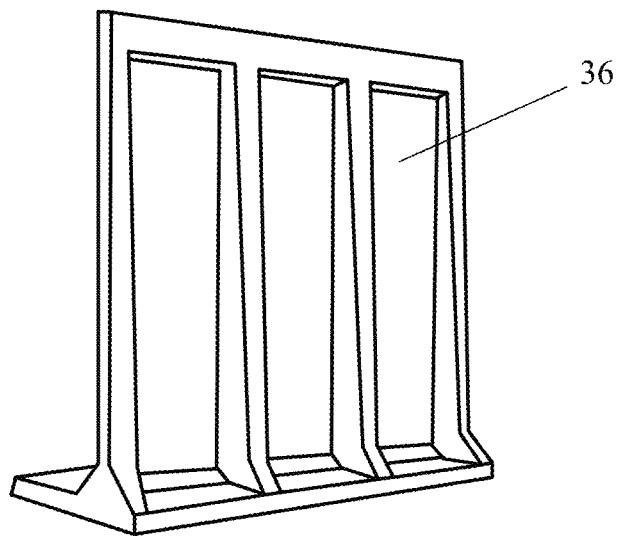
FIG. 2A shows schematically a wall unit for a modular methane digester in an embodiment of the present invention.
Figure 2B:
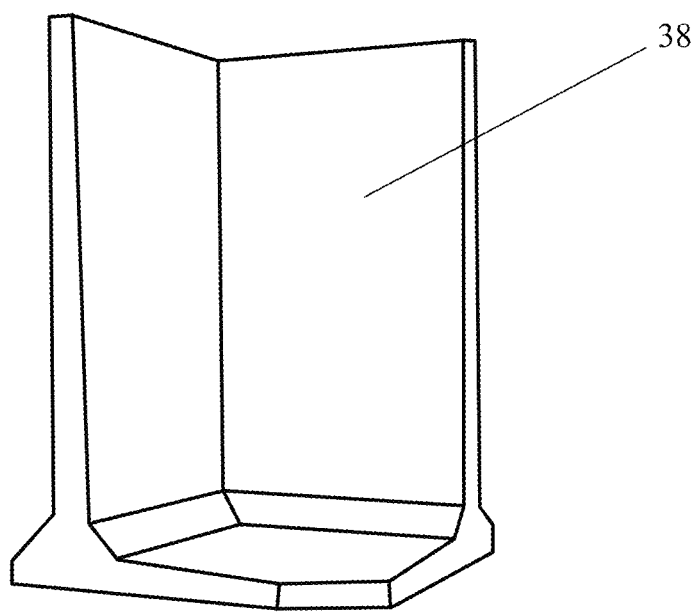
FIG. 2B shows schematically a corner unit for a modular methane digester in an embodiment of the present invention.

FIGS. 2A and 2B show a wall unit 36 and a corner unit 38, respectively, for the modular methane digester. The wall unit 36 and the corner unit 38 are preferably made of concrete. In one embodiment, the wall unit has a base area of about four feet by about seven and a half feet and a height of about eight and a half feet, and the corner unit has a base area of about five feet by about five feet and a height of about eight and a half feet. The wall units and corner units are preferably placed with no foundation either directly on the ground or on a layer of insulation. The modular methane digester may be sized to fit the size of the farm by choosing the appropriate number of wall and corner units.

FIG. 3 shows a portion of the interior of a completed modular methane digester structure 26. The wall units 36 and the corner units 38 are rectangularly arranged with air-tight seals between the units. Headers 42 mounted above the units 36, 38 integrate the units. A PVC scaffold 44 mounted on top of the headers 42 supports the membrane roof structure 46. The concrete floor slabs 48 slope downward toward a trough 50 between the slabs 48, to which excess liquid percolate drains. The trough 50 is preferably filled with marble gravel, which, by nature of its sensitivity to sulfidation, collects, absorbs, and neutralizes excess hydrogen sulfide. The trough 50 preferably has a drain so that the liquid percolate may be re-collected in the percolate storage tank 18 and re-used, stored, or disposed of. The percolate dispersal system 52 is mounted to the headers 42 on the two side walls of the methane digester. PVC piping supplies the liquid stage to a plurality of nozzles 54 spaced along the piping, which direct the liquid stage toward the solid stage stacked on the floor of the methane digester.

Figure 4:
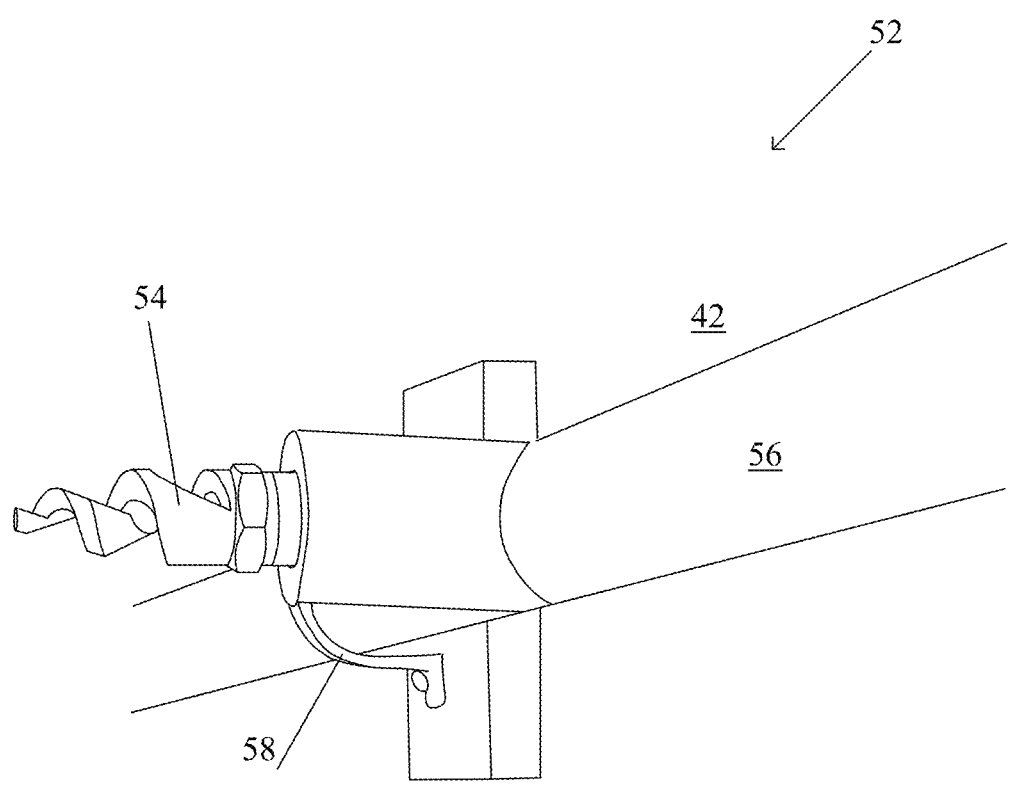
FIG. 4 shows schematically a portion of a percolator dispersal system in an embodiment of the present invention.

FIG. 4 shows a more detailed view of a nozzle 54 of the percolate dispersal system 52. The nozzle 54 is preferably a no-clogging type of nozzle of a coated metal alloy that resists sulfidation, the corrosive action of gaseous hydrogen sulfide in a moist environment. The nozzles are preferably threaddedly mounted into the PVC piping banks 56 along the headers 42 of the methane digester. The PVC piping banks 56 are preferably mounted to the headers 42 by a plurality of brackets 58 spaced along the headers 42.

Figure 5A:
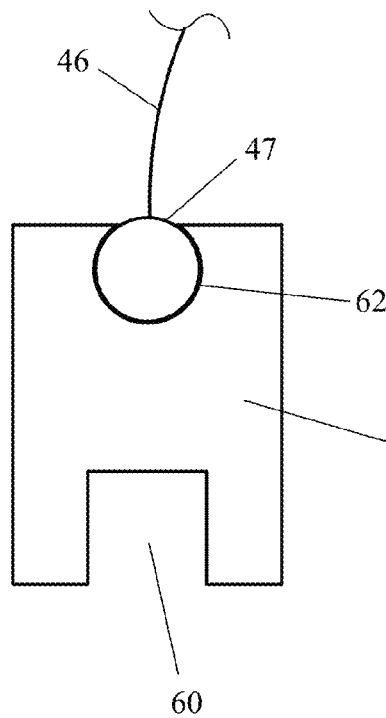
FIG. 5A shows schematically a cross sectional view of a header for a methane digester in an embodiment of the present invention.
Figure 5C:
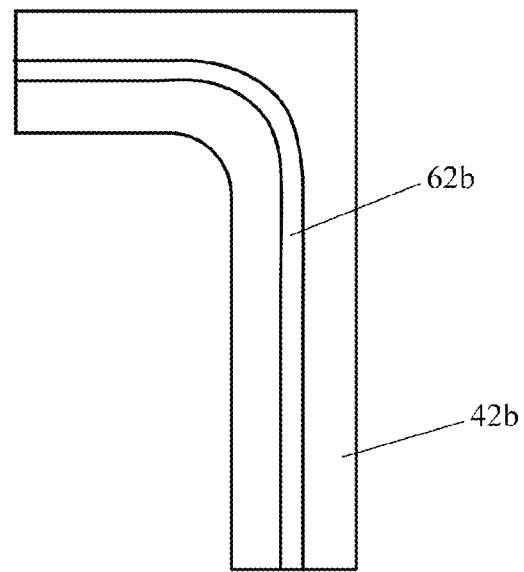
FIG. 5C shows schematically a top view of a corner header for a methane digester in an embodiment of the present invention.
Figure 5B:
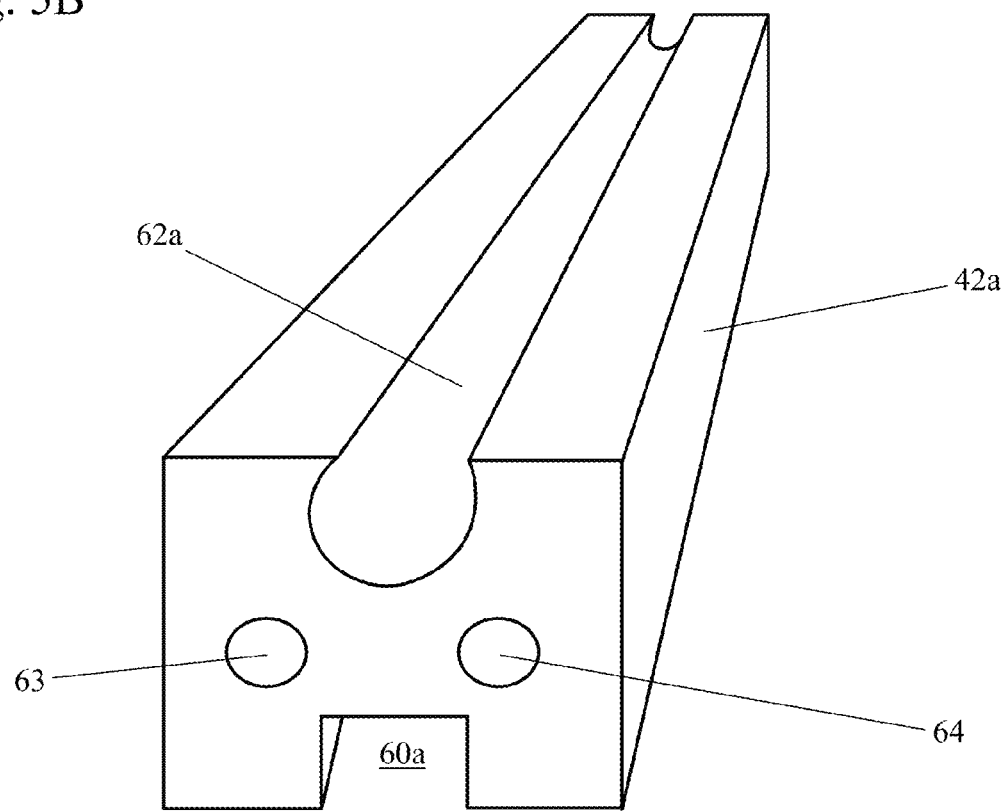
FIG. 5B shows schematically a perspective view of a straight header for a methane digester in an embodiment of the present invention.

FIG. 5A through FIG. 5C show the concrete headers 42, 42a, 42b that are mounted to the tops of the wall units 36 and the corner units 38, as shown in FIG. 3. The straight headers 42a are used in the straight wall portions of the methane digester and the corner headers 42b are used in the corners of the methane digester. The headers are preferably pre-cast out of concrete. Each header includes a key 60, 60a on the bottom to receive the tops of the wall units or corner units. Each header also includes a trough 62, 62a, 62b for receiving a membrane and an air hose to form an airtight seal between the concrete and the membrane roof. The trough is preferably epoxy-coated to receive expandable air-lock tubing. The headers 42, 42a, 42b also preferably include countersunk holes 63, 64 for receiving connector rods to hold neighboring headers together. The countersunk holes 63, 64 may go the length of the straight headers or may go through only a portion of the length. The countersunk holes preferably only go part of the way through the corner headers. FIG. 5A shows the expandable tubing 47 pushed into the epoxy-coated trough 62, which "pinches" the membrane into the circular fixture. The expandable tubing 47 goes around the edge of the membrane roof 46, and inflation of the tubing to 40-60 psi effectively crimps the membrane in an air-lock fashion. The membrane is readily opened by deflating the tubing.

Figure 6:
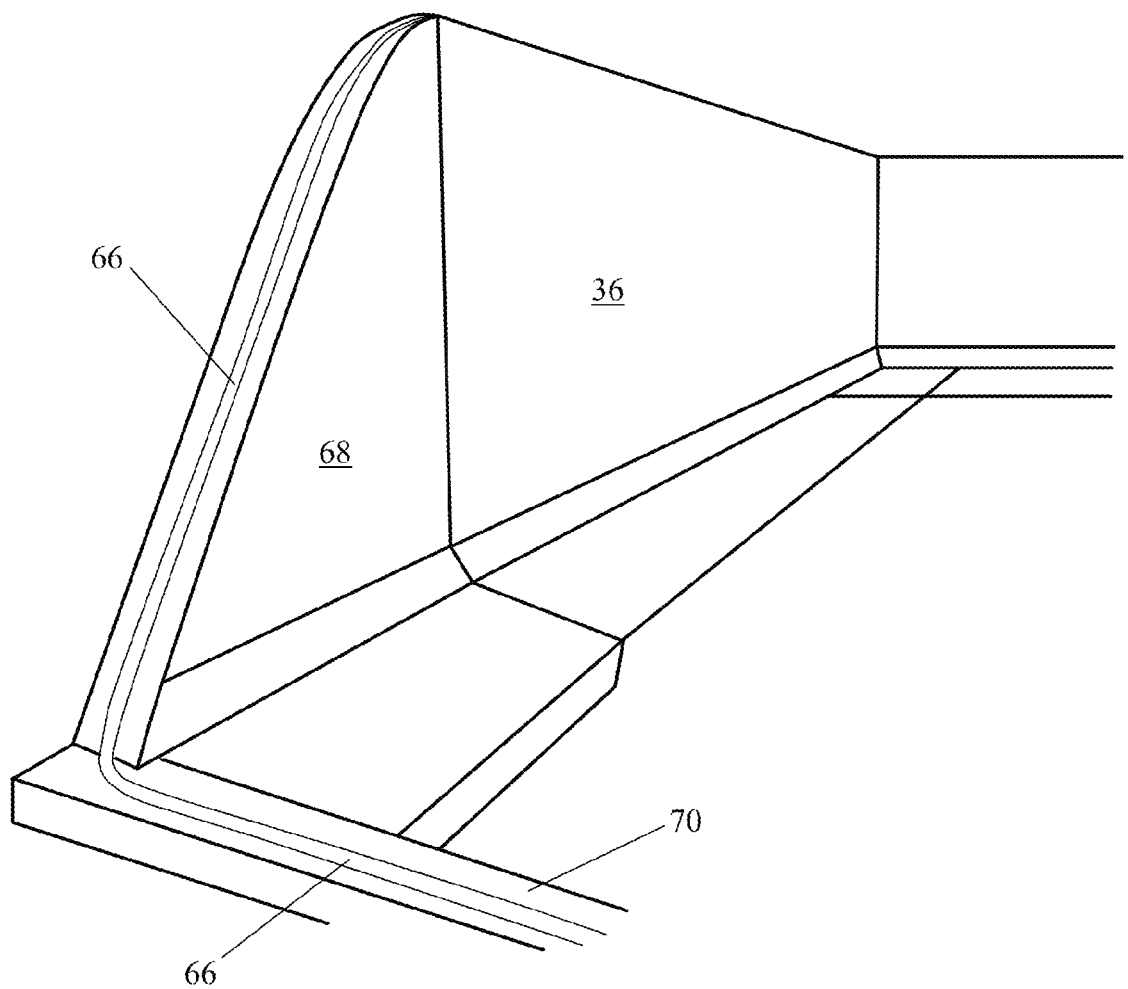
FIG. 6 shows schematically a front perspective view of a membrane door closure fixture of a methane digester in an embodiment of the present invention.

FIG. 6 shows an air lock channel 66 extending down the modular front unit 68 to the concrete footers 70 at the front of the methane digester, thereby forming a continuous channel 66 around the top of the concrete portion of the methane digester. The rubber membrane of the methane digester is pressed into the air lock channel, the pressure-expandable hosing is inserted, and the hosing is then inflated, which pinches or crimps to form a seal. In some embodiments, the hosing is inflated to a pressure of about 60 psi. Since the entire facility is preferably operated at only 4 ounces of pressure (0.25 psi max), the air sealing of the membrane being pinched into the trough under greater pressure is very effective.

The curved epoxy-coated trough comes down the modular front unit to enable the continuous sealing of the expandable tubing to pinch the membrane. In practice, the trough is preferably formed by the concrete straight-headers, corner-headers, front sloping walls, and front floor footers to provide a continuous seal all the way around the methane digester. The positioning and sizing of the epoxy-coated trough in the concrete forms (straight-headers, corner-headers, front sloping walls, and front floor footers) is preferably such that by applying simple air pressure, as by a foot pump, the air-expandable tubing, which is preferably capable of withstanding up to 200 psi pressure, is pushed into the trough and captures and pinches the membrane cover.

The membrane is preferably tightened and formed to the curvilinear shape of the facility by placing or "tucking" folds at appropriate points along the sides of the digester. These folds are readily accommodated by the epoxy-lined troughs in which a double-fold membrane is created. The inflation of the air-tubing effectively compresses the fold and air-seals it.

The resulting structure is a modular, scalable, high-solids methane digester that is sealed by use of a rubber membrane cover, which is readily opened by temporarily releasing the air pressure in the tubing, at which point the trough releases the expandable tubing, which in turn allows the membrane to be opened.

In some embodiments, the side and back portions of the air lock trough are covered permanently with white PVC boards, and access to the digester is provided, as needed, in the front of the digester. In some embodiments, an air-pressure supply-line extends along the sides above the air lock trough to the air lock trough portion along the back wall of the digester. The air-pressure supply-line is preferably attached to a conventional air-pressure regulator from a conventional small-scale air compressor, which keeps the air-lock trough inflated and fully sealed.

The membrane roof is preferably sized such that the entire membrane enclosure may expand up to the full height of the insulated, enclosed building and reacts naturally to changes in barometric pressure, heating production, and gas production to "expand and contract" without a detrimental effect on overall performance.

Figure 7A:
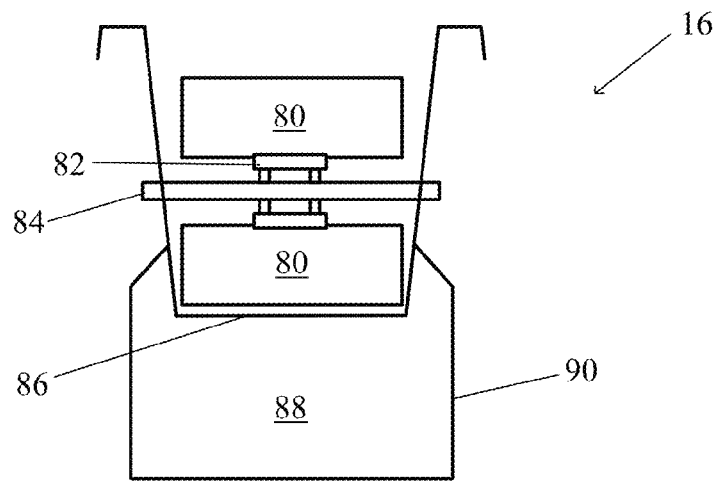
FIG. 7A shows schematically a cross sectional view of a separator-conveyor dewatering device in an embodiment of the present invention.
Figure 7B:
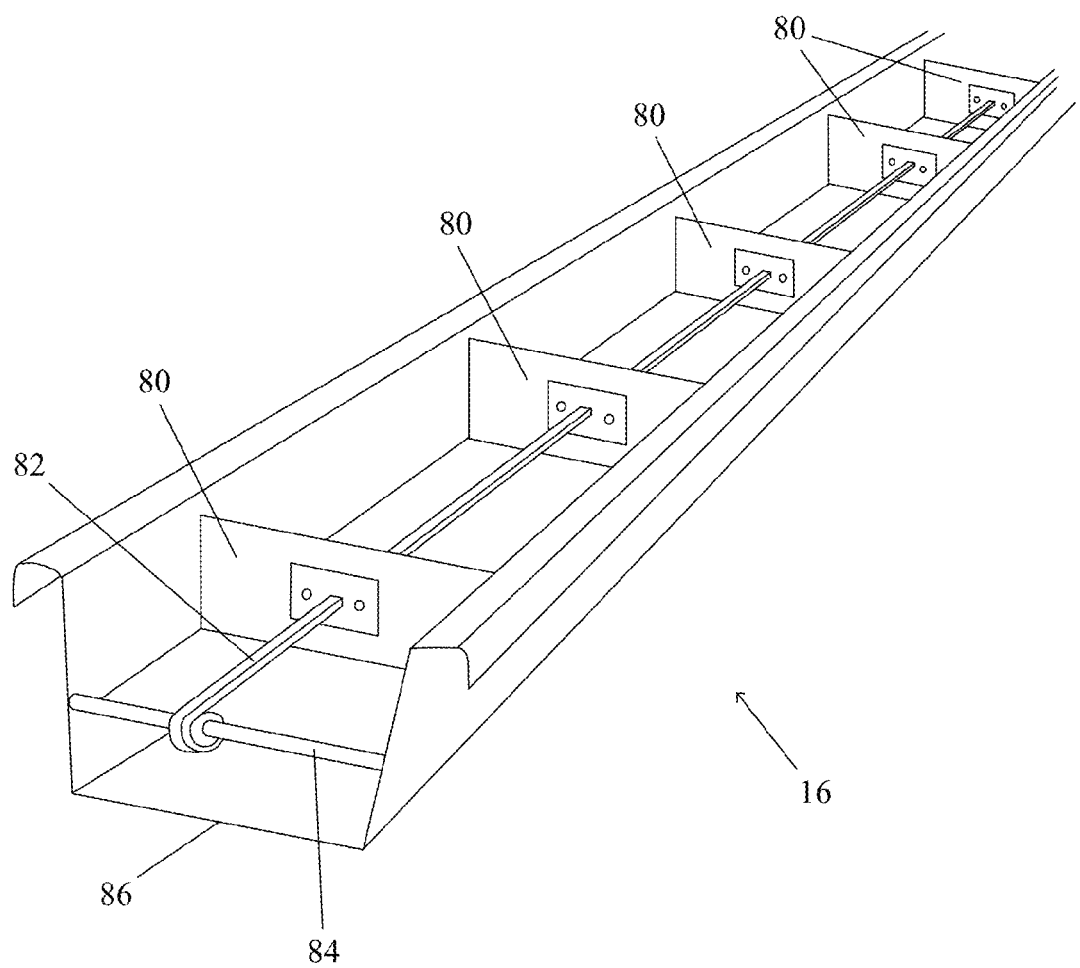
FIG. 7B shows schematically a perspective view of the separator-conveyor dewatering device of FIG. 7A.

FIG. 7A and FIG. 7B show a solids conveyor-separator 16. A plurality of paddles 80 are cycled by a conveyor 82 to bring solid materials from one end of the conveyor-separator 16 to the other. The paddles 80 are preferably made of high-durability flexible rubber. The conveyor 82 is driven by an axle 84. The conveyor 82 is preferably a chain driven by a sprocket driven by the axle 84, preferably driven by a hydraulic motor, but other drive mechanisms may alternatively be used, including, but not limited to, a belt and drive wheel. A perforated floor 86 separates the paddles 80 from a lower chamber 88 formed within a housing 90. In some embodiments, the perforations in the perforated floor 86 are holes $3/32$-inch to $1/8$-inch in size. As the production animal waste is transported up the solids conveyor-separator 16 by the paddles 80, the liquid portion tends to drain off the paddles 80 and is then dropped or pressed through the perforated floor 86 to the lower chamber 88, where it collects and flows back down to the bottom of the conveyor-separator 16. The solid portion tends to remain on the conveyor such that the solid portion reaching the top of the conveyor-separator 16 has a much higher solid content and the liquid drained through the perforated floor has a much higher liquid content than the original production animal waste.

Excess moisture normally present in freshly-voided manures, which mixes with wash water in barns, typically results in a low-solids manure, including less than 12% solids and at least 78% moisture. The medium-efficiency solids conveyor-separator removes excess moisture such that the manure material is stackable in such a modular, scalable, high-solids on-farm digester.

Stacking of dairy manure normally requires at least 20% total solids before the manure remains in form. Once the solids content is raised, the manure is transported to the digester as a solid and may be loaded and stacked such that moisture flows through via a percolation process, to reach the percolator trough and then into the storage tanks, from which it is redistributed to the stacked mass by the recirculation spray nozzle system.

A series of flexible paddles are drawn across a permeable surface, which, drawing the manure along, cause moisture to squeeze out through the holes and solids to be pushed to a drop at the other end of the conveyor-separator and ejected into a pile. The two-chamber device preferably pushes semi-solid manure in the upper chamber across a permeable grid with specific $3/32$" to $1/8$" holes that permit liquid to pass through by squeegee action caused by the movement across the surface of semi-flexible rubber paddles. The lower chamber collects the liquid drainage and directs it downwards, by nature of the slope of the device, to a trough that takes it to the storage lagoon. To facilitate and enhance the removal of water from the moving stream of manure passing over the conveyor, compressed air may be pulsed via an air-knife device onto the surface of the perforated floor 86 such that liquid that is adhering to solid particles, such as macerated hay and plant stem material that are present in the manure, is made less resistant to drainage by the air force from an ordinary stream of compressed air and pushed out through the $3/32$-inch to $1/8$-inch holes.

Figure 8:
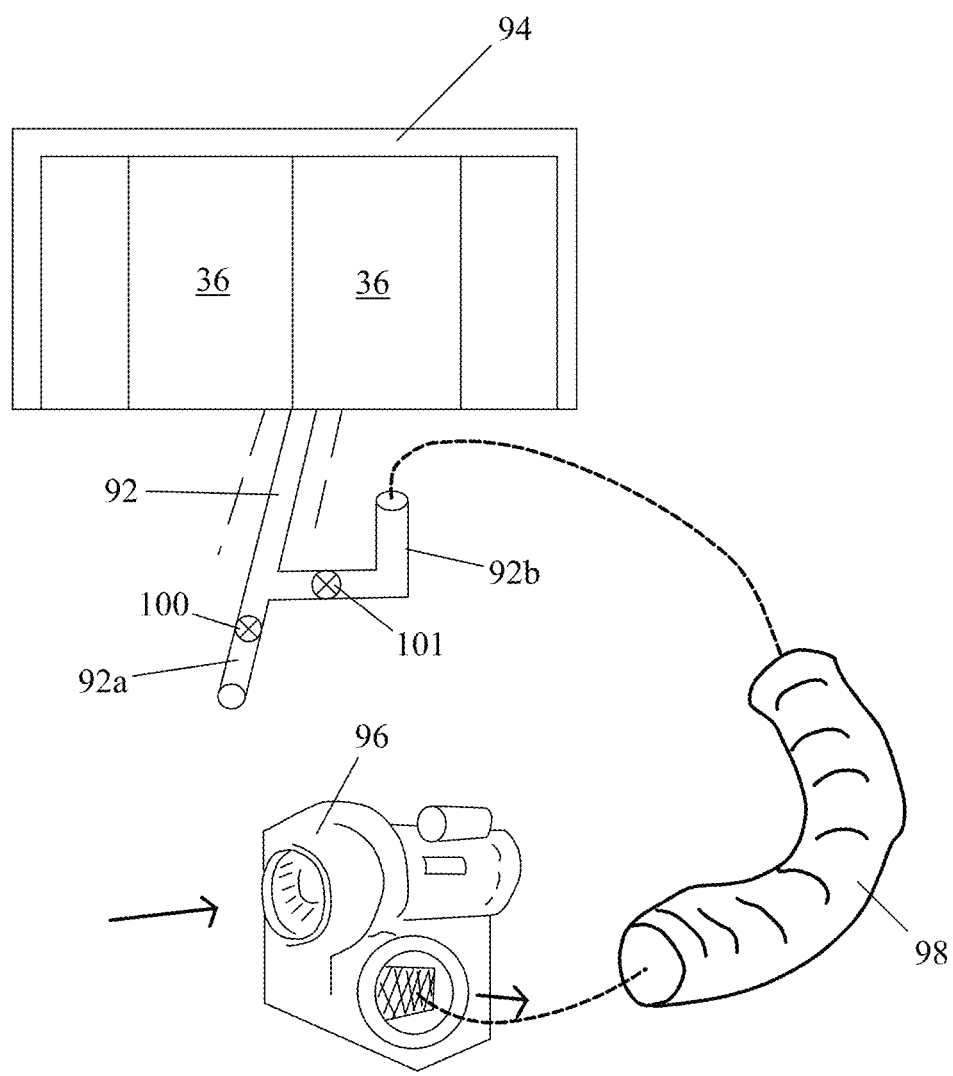
FIG. 8 shows schematically an exploded view of a reverse air pump system for a methane digester in an embodiment of the present invention.

FIG. 8 shows a reverse air pump system for a methane digester with a reverse air pump system. The liquid portion drained from the conveyor-separator 16 flows into a pipe 92 exiting under the rear wall 94 of the methane digester. The pipe 92 splits into a portion 92a that transfers the liquid portion to the percolate-storage unit 18 and a portion 92b that connects to an air blower 96 via a flexible connector pipe 98. A pair of air-tight valves 100, 101, preferably gate valves, on the pipes 92a, 92b permit, constrict, or prevent flow through the pipes 92a, 92b according to whether percolate is moving through the pipes or air is being supplied.

The air blower unit connects to a side port and pushes oxygen-laden air into the digester both before and after the digestion process. This air sustains the exothermic (heat-producing) reactions to warm the mass before digestion and refreshes the mass to an aerobic compostable state after digestion. The blower is preferably sized to accommodate the volume mass of manure digester mix at a static pressure (SP) of up to 3" for a 10- to 15-minute air exchange cycle. The air is preferably supplied from outdoors and is pumped by the low-pressure, high-flow rate blower to the digester. The air flows to the liquid drainage pipe, where it is pushed into the digester by way of the trough on the floor of the digester.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of modular construction of a methane digester facility comprising the steps of:
    placing a plurality of prefabricated portable concrete panels to form a pair of opposing side walls and a back wall connected to the side walls by corner concrete panels;
    placing a modular concrete angled front piece at a front end of each side wall to produce a sloped door inset piece;
    placing a row of headers on the side walls and the back walls;
    placing a plurality of footers in a row between the modular concrete angled front pieces, wherein troughs formed in the tops of the headers, the front pieces, and the footers form a continuous sealing channel around the top of the methane digester facility; and
    sealing an interior space of the methane digester using a flexible membrane roof having inflatable ends insertable into the continuous sealing channel.

2. The method of claim 1 further comprising the step of mounting a scaffold on top of the headers such that the scaffold supports the flexible membrane roof.

3. The method of claim 1 further comprising the step of mounting piping including a plurality of percolate dispersal nozzles along an inward-facing side of the headers.

4. The method of claim 1 further comprising the step of integrating a separator-conveyor dewatering device into a front end of the methane digester facility.

5. The method of claim 4, wherein the separator-conveyor dewatering device comprises:
    an upper housing;
    an infinite chain;
    a plurality of flexible paddles mounted to the infinite chain;
    a pair of axles mounted to the upper housing;
    a drive mechanism driving the infinite chain around the axles;
    a lower trough supporting the upper trough; and
    a perforated floor separating the upper trough from the lower trough, the perforated floor having a plurality of through-holes permitting drainage of liquid from the upper trough to the lower trough.

6. The method of claim 5, wherein the upper trough and the lower trough are sloped such that liquid draining into the lower trough runs down to a lower end of the lower trough.

7. The method of claim 5, wherein the paddles transporting a semi-solid liquid manure from a lower end of the upper trough toward an upper end of the upper trough act as squeegees against the perforated floor to separate a substantially liquid portion of the semi-solid liquid manure from a substantially solid portion of the semi-solid liquid manure.

8. The method of claim 7, wherein the substantially solid portion of the semi-solid liquid manure exits the upper end of the upper trough having a higher solid content than when the semi-solid liquid manure entered the lower end of the upper trough.

9. The method of claim 5, wherein the separator-conveyor dewatering device further comprises an air-knife pulsing compressed air onto the surface of the perforated floor such that liquid adhering to solid particles is pushed out through the perforations.

* * * * *